United States Patent
Dufek

(10) Patent No.: US 9,902,590 B2
(45) Date of Patent: Feb. 27, 2018

(54) RETRACTABLE-EXPANDABLE RESTRAINT DEVICE

(71) Applicant: Qwik Cuff LLC, Daytona Beach, FL (US)

(72) Inventor: David A. Dufek, Daytona Beach, FL (US)

(*) Notice: Subject to any disclaimer, the term of this patent is extended or adjusted under 35 U.S.C. 154(b) by 533 days.

(21) Appl. No.: 14/328,332

(22) Filed: Jul. 10, 2014

(65) Prior Publication Data

US 2015/0013690 A1    Jan. 15, 2015

Related U.S. Application Data

(60) Provisional application No. 61/844,672, filed on Jul. 10, 2013.

(51) Int. Cl.
*A61F 5/37* (2006.01)
*B65H 75/44* (2006.01)
*A01K 27/00* (2006.01)
*E05B 75/00* (2006.01)

(52) U.S. Cl.
CPC ....... *B65H 75/4486* (2013.01); *A61F 5/3761* (2013.01); *A61F 5/3769* (2013.01); *B65H 75/446* (2013.01); *B65H 75/4431* (2013.01); *A01K 27/003* (2013.01); *A01K 27/004* (2013.01); *E05B 75/00* (2013.01)

(58) Field of Classification Search
CPC ........ A61F 5/37; A61F 5/3761; A61F 5/3769; E05B 75/00; A01K 27/00; A01K 27/003; A01K 27/004

USPC ..... 128/869, 878, 879; 70/16; 119/769, 770, 119/772, 792, 794–796, 798
See application file for complete search history.

(56) References Cited

U.S. PATENT DOCUMENTS

| | | | |
|---|---|---|---|
| 4,422,455 A | 12/1983 | Olsen | |
| 4,621,589 A * | 11/1986 | Thinnes | A01K 27/004 119/770 |
| 6,474,588 B2 * | 11/2002 | Valverde | B63B 35/816 114/254 |
| 7,210,317 B2 | 5/2007 | Beane et al. | |
| 7,340,926 B2 | 3/2008 | Kim et al. | |
| 7,866,617 B2 * | 1/2011 | Kleitsch | A61M 5/1417 248/228.5 |
| 8,418,659 B2 * | 4/2013 | Harruna | A01K 27/004 119/796 |
| 2010/0031709 A1 | 2/2010 | Kim et al. | |
| 2012/0085135 A1 | 4/2012 | Louden | |
| 2013/0047934 A1 * | 2/2013 | Morris | B60R 22/10 119/771 |

* cited by examiner

Primary Examiner — Keri J Nelson

(57) ABSTRACT

A restraint device and method of using a restraint device including an outer body, a storage wheel, a line, a first and second connector, and a release mechanism. The storage wheel may be carried by an internal portion of the outer body. The line may be carried by the storage wheel and moveable between an extended position and a retracted position. The first connector may be connected to a portion of the outer body and adapted to be connected to at least a portion of an external structure. The second connector may be detachably connected to an end portion of the line and adapted to be detachably connected to a restraint. The release mechanism may be carried by the outer body and in mechanical communication with the storage wheel. The release mechanism may be moveable between an engaged position and a released position.

19 Claims, 14 Drawing Sheets

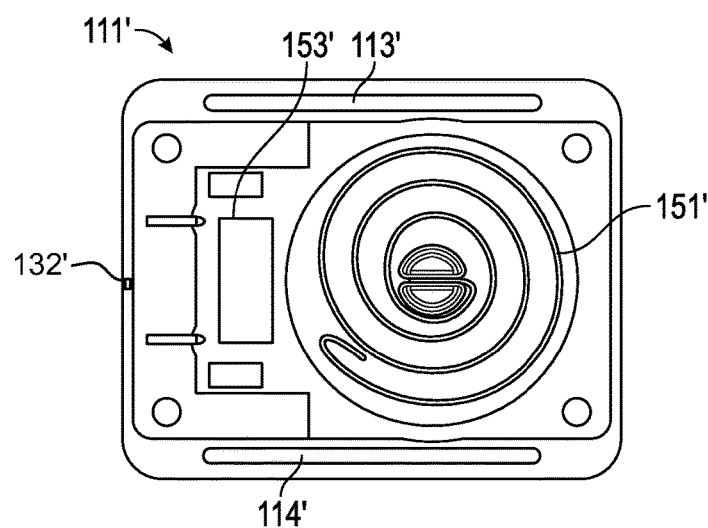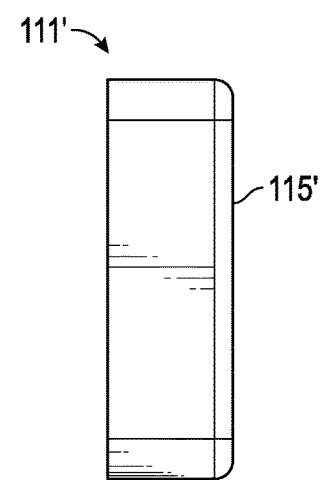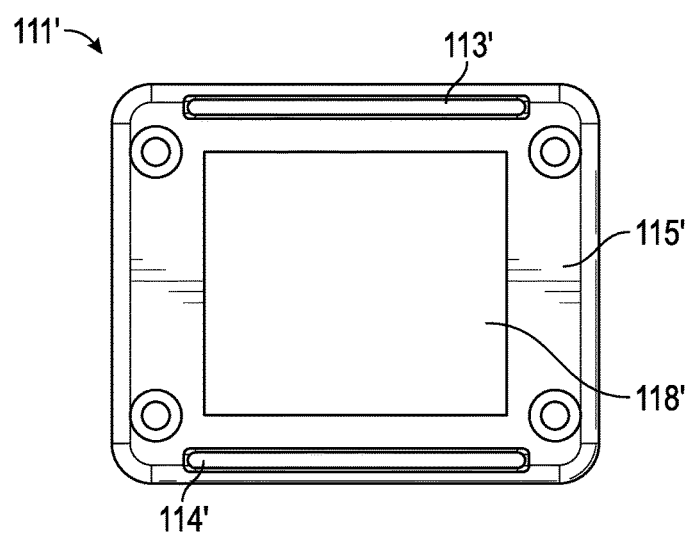
FIG. 7     FIG. 8
FIG. 9

RETRACTABLE-EXPANDABLE RESTRAINT DEVICE

RELATED APPLICATIONS

This application claims the benefit under 35 U.S.C. § 119(e) of U.S. Provisional Patent Application Ser. No. 61/844,672 filed on Jul. 10, 2013 and titled RETRACTABLE-EXPANDABLE RESTRAINT DEVICE, the entire content of which is incorporated herein by reference.

FIELD OF THE INVENTION

The present invention relates to the field of restraining devices and, more specifically, to restraining devices used in connection with patient care.

BACKGROUND

Restraining devices used in connection with patient care are generally limited in use as they are fixed, i.e., they cannot be easily or quickly adjusted in size or length. The restraining devices often require untying or cutting of the line and then retying or reconnecting the restraining device. Of the few restraining devices that can be adjusted, many require three or four persons to force a person's hands or feet together or to force a person's hands, feet, or body to another object in order to restrain the person. These types of restraining devices are generally not for use with patients, but more suitable for prisoner use. Restraining devices also often incorporate a lock and key mechanism to release the person from a restraint, which can be problematic if rapid release is necessary and the key is not readily available. Accordingly, there is a long felt need for a restraining device that requires less manpower in restraining a person and still has a rapid release ability that does not cause destruction or damage of the device.

U.S. Pat. No. 4,422,455 to Olsen discloses a restraint device and includes an adjustable strap and a quick release receptacle and clasp member. It further includes an adjustable cuff that girdles the arm of a patient. The device does not include a means of connection to other types of cuffs and involves an adjustable buckling system that can be complicated to use, can come apart, and only expands or retracts using force.

U.S. Pat. No. 7,340,926 to Kim et al. discloses a restraint device with two bracelets at either end of a central holder. One bracelet is retractable and extendable and one bracelet is able to girdle an object. The device does not allow a user to retract and extend the former bracelet when the second bracelet is engaged, however. Additionally, the first bracelet is a type of handcuff that can cause the restrained individual discomfort and harm and does not contain a quick release function in case of emergency or other need. Furthermore, the device cannot be manually retracted and a motor cannot be used to retract/extend the first bracelet.

U.S. patent application Ser. No. 12/320,857 by Kim et al. discloses a set of handcuffs with two bracelets at either end of a control device. One bracelet is retractable and extendable and both bracelets are able to girdle a subjects hand or foot. The device does not allow a user to retract and extend the retractable/extendable bracelet when the other bracelet is engaged, however. Furthermore, the mechanism for retraction is a spring. The device cannot be manually retracted and a motor cannot be used to retract/extend either bracelet. The device does not contain a quick release function and it is only used to bring the person's hands or feet together, not to attach to a stretcher, bed, wheelchair, or other object. Additionally, the bracelets are a type of handcuffs that can cause the restrained individual discomfort and harm and does not contain a quick release function in case of emergency or other need.

U.S. Pat. No. 7,210,317 to Beane et al. discloses a pair of opposing restraint members and a housing. The first restraint member is attached to a thin, flexible, high tensile belt, cord or cable tether which is attached to a controllably-ratcheted, winding-rewinding spool within the housing. The second restraint member is directly attached to the housing. When operated by a user, the first restraint member can be extended or retracted by a controllable ratchet-pawl release mechanism or a rewinding mechanism. Once actuated, the tether can no longer be extended, only retracted. The device does not contain a quick release function, is only used to bring the person's hands or feet together not to attach to a stretcher, bed, wheelchair, or other object, and is intended for law enforcement purposes.

U.S. patent application Ser. No. 13/172,688 by Louden discloses a set of handcuffs, including two cuffs and a cable. One cuff is secured to the wrist of an individual and the release is operated to expand the handcuffs so that the second cuff can be secured to the other wrist of the individual. The handcuffs can be expanded and retracted. The device does not contain a quick release function, is only used to bring the person's hands or feet together, not to attach to a stretcher, bed, wheelchair, or other object, and is intended for law enforcement purposes. Additionally, the bracelets are a type of handcuff that can cause the restrained individual discomfort and harm and does not contain a quick release function in case of emergency or other need.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

In view of the foregoing, it is therefore an object of the present invention to provide an improved restraint device. It is also an object of the present invention to provide a restraint device that can be easily used to restrain a patient as may be necessary. It is further an object of the present invention to provide a restraint device that can be readily cleaned. It is still further an object of the present invention to provide a restraint device that is comparable for a patient, and that can be readily attached to an external structure. The restraint device according to embodiments of the present invention may not necessarily require use of a key, which could be lost or unavailable when needed. Additionally, the restraint device according to embodiments of the present invention may accommodate larger or stronger individuals where another restraint device may not expand or may not properly fit such an individual. Furthermore, the restraint device according to embodiments of the present invention may be easier to locate since it will preferably be positioned on a stretcher, bed, wheelchair, or other object/external structure.

These and other objects, features and objectives according to the present invention are provided by a restraint device that may include an outer body, a storage wheel carried by an internal portion of the outer body, and a line that may be carried by the storage wheel and moveable between an extended position and a retracted position. The retracted position is defined as the line being carried by the storage wheel and positioned substantially internal to the outer body. The extended position is defined as the line being at least partially carried by the storage wheel and having at least a portion extending exterior to the outer body.

The restraint device may also include a first connector connected to a portion of the outer body and adapted to be connected to at least a portion of an external structure. The restraint device may further include a second connector detachably connected to an end portion of the line and adapted to be detachably connected to a restraint. A release mechanism may be carried by the outer body and may be in mechanical communication with the storage wheel. The release mechanism is moveable between an engaged position and a released position. The engaged position is defined as the release mechanism engaging a portion of the storage wheel to prevent rotation thereof so that the line is prevented from moving between the extended position and the retracted position. The released position is defined by the release mechanism being disengaged from the storage wheel so that the line is movable between the extended position and the retracted position.

The outer body may include a first elongate passageway. The first connector may be positioned through the first elongate passageway so that an end of the first connector is unable to pass through the first elongate passageway. The outer body may also include a first side and a second side opposing the first side. The first side may have the first elongate passageway and the second side may have a second elongate passageway. The first connector may be adapted to be positioned through the first and second elongate passageways.

The restraint device according to embodiments of the present invention may include a pad attached to a back section of the outer body. The pad may be made of neoprene, rubber, plastic, or foam material. The release mechanism may be positioned on the outer body opposite the back section. The first connector may include a fastener adapted to fasten the outer body to the external structure, and the second connector may include a fastener adapted to fasten the second connector to the restraint. The restraint may be adapted to be secured around a portion of a person's anatomy.

The restraint device according to embodiments of the present invention may also include a ratchet mechanism connected to the storage wheel. The ratchet mechanism may be provided by a spring-controlled ratchet mechanism or a user-controlled ratchet mechanism. When the ratchet mechanism is engaged, the ratchet mechanism prevents motion of the line. The line may be provided by a steel material, a metal material, a metal alloy, a plastic material, a nylon material, a synthetic material, or a fibrous material. Further, in some embodiments, the line may be coated with a nylon material, a flame resistant material, a high heat resistant material, a rubber material, a urethane material, or a plastic material.

The restraint device according to embodiments of the present invention may also include a reservoir that is adapted to contain a substance to be deposited on at least a portion of the line. The substance may, for example, have anti-bacterial, disinfecting, cleaning, and/or lubricating properties.

In some embodiments, the restraint device may also include a motor carried by the outer body and a power supply in communication with the motor. The motor may be in mechanical communication with the storage wheel, and engagement of the motor may cause the storage wheel to turn so that the line may be moved between the extended position and the retracted position.

A method aspect of the present invention is for using the restraint device. The method may include connecting the first connector to an external structure, connecting the second connector to the restraint, and moving the release mechanism between an engaged position and a released position.

BRIEF DESCRIPTION OF THE DRAWINGS

FIG. 7 is a side elevation view of a first portion of an outer body of a restraint device according to an alternate embodiment of the present invention.

FIG. 8 is a rear elevation view of the first portion of the outer body of the restraint device illustrated in FIG. 7.

FIG. 9 is a side elevation view of a back section of the first portion of the outer body of the restraint device illustrated in FIG. 7.

DETAILED DESCRIPTION OF THE INVENTION

Figure 1:
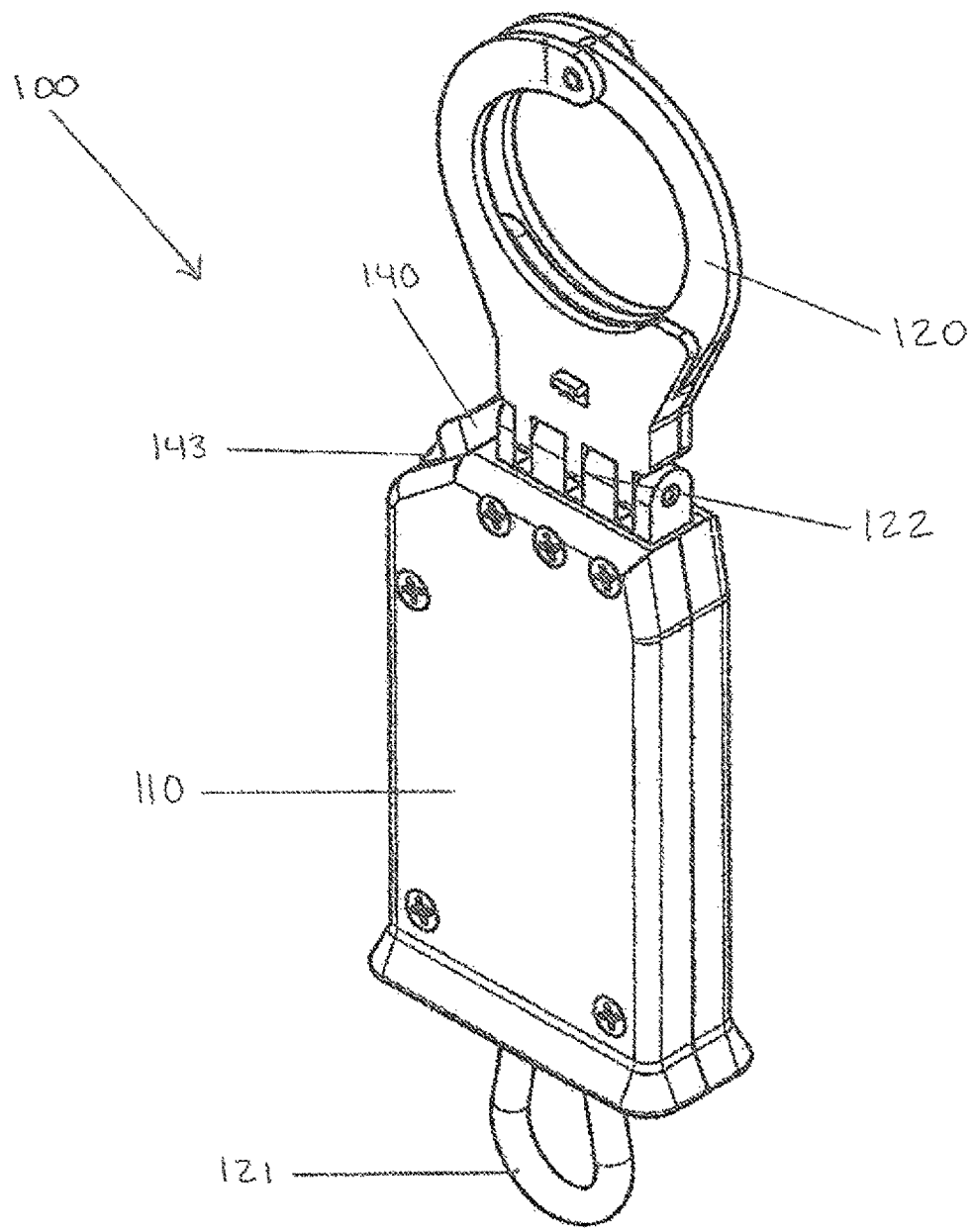
FIG. 1 is a perspective view of a restraint device according to an embodiment of the present invention.
Figure 2:
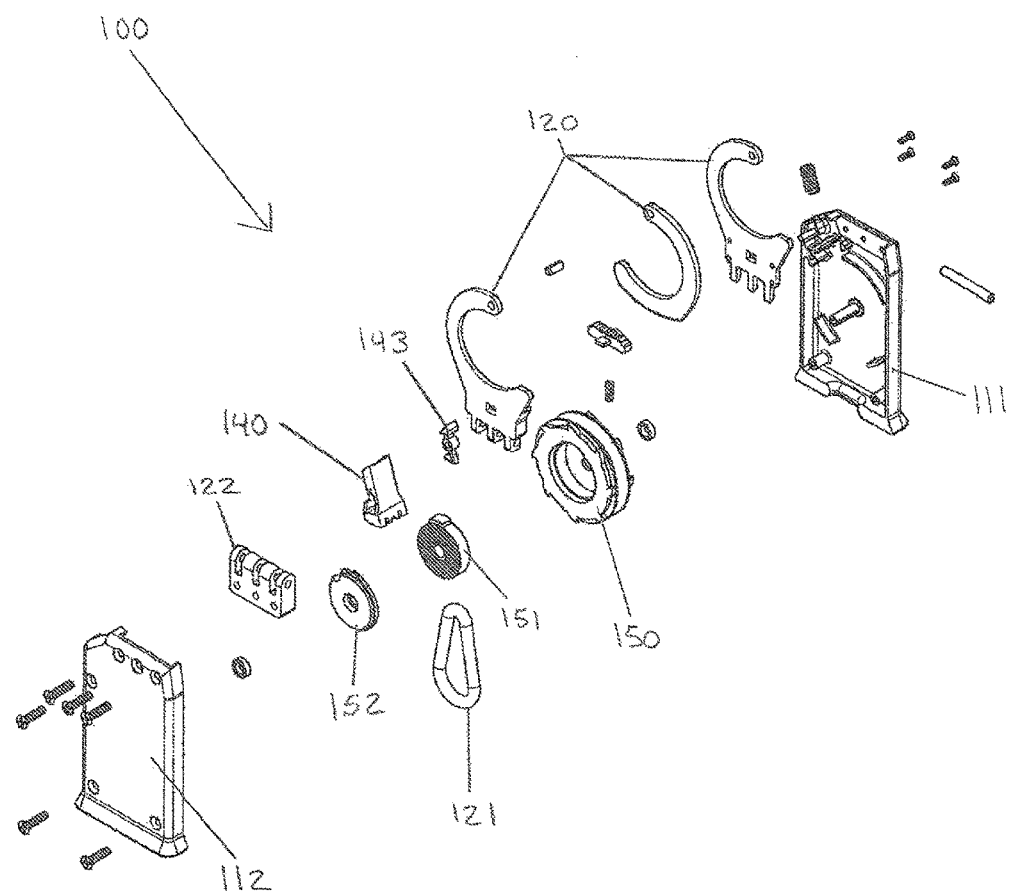
FIG. 2 is an exploded perspective view of the restraint device illustrated in FIG. 1.
Figure 3:
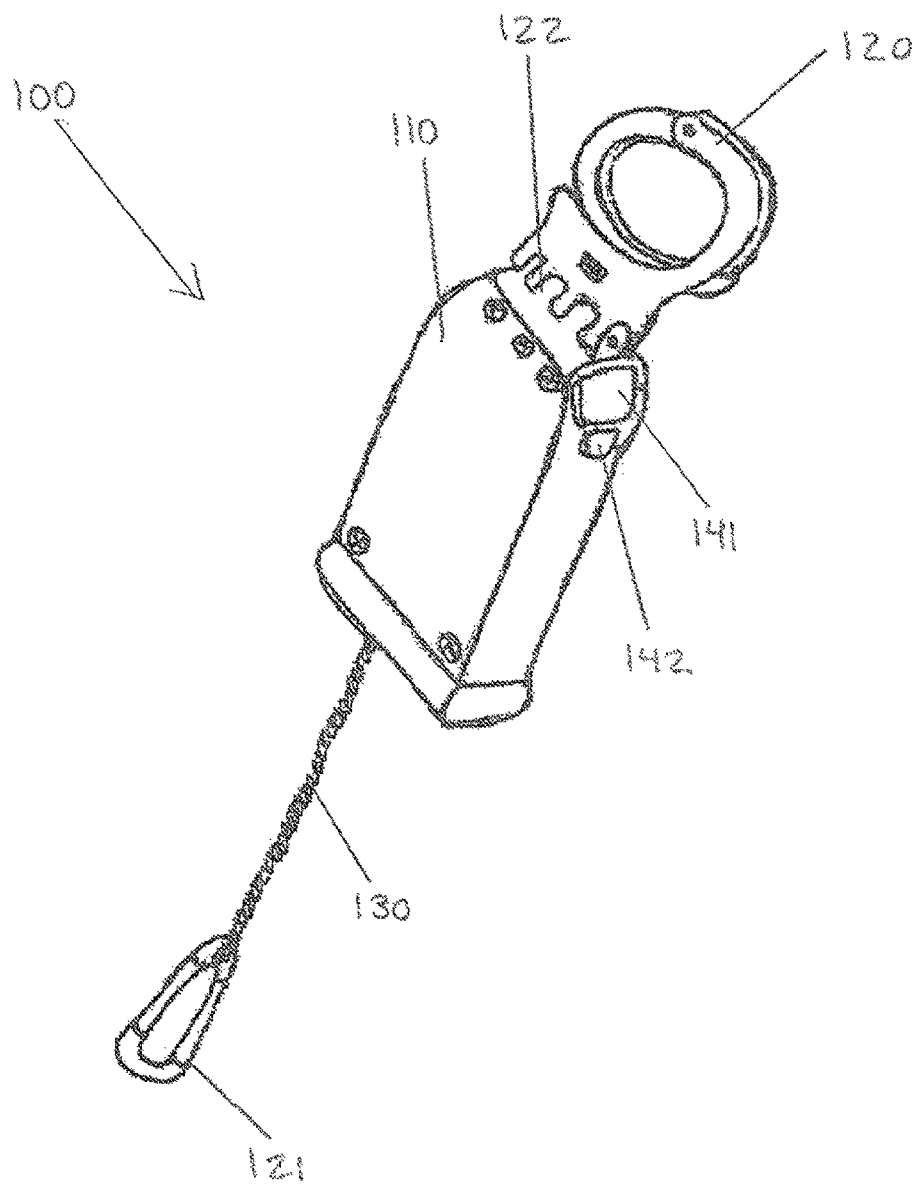
FIG. 3 is a perspective view of the restraint device illustrated in FIG. 1 showing the line in an extended position.
Figure 4:
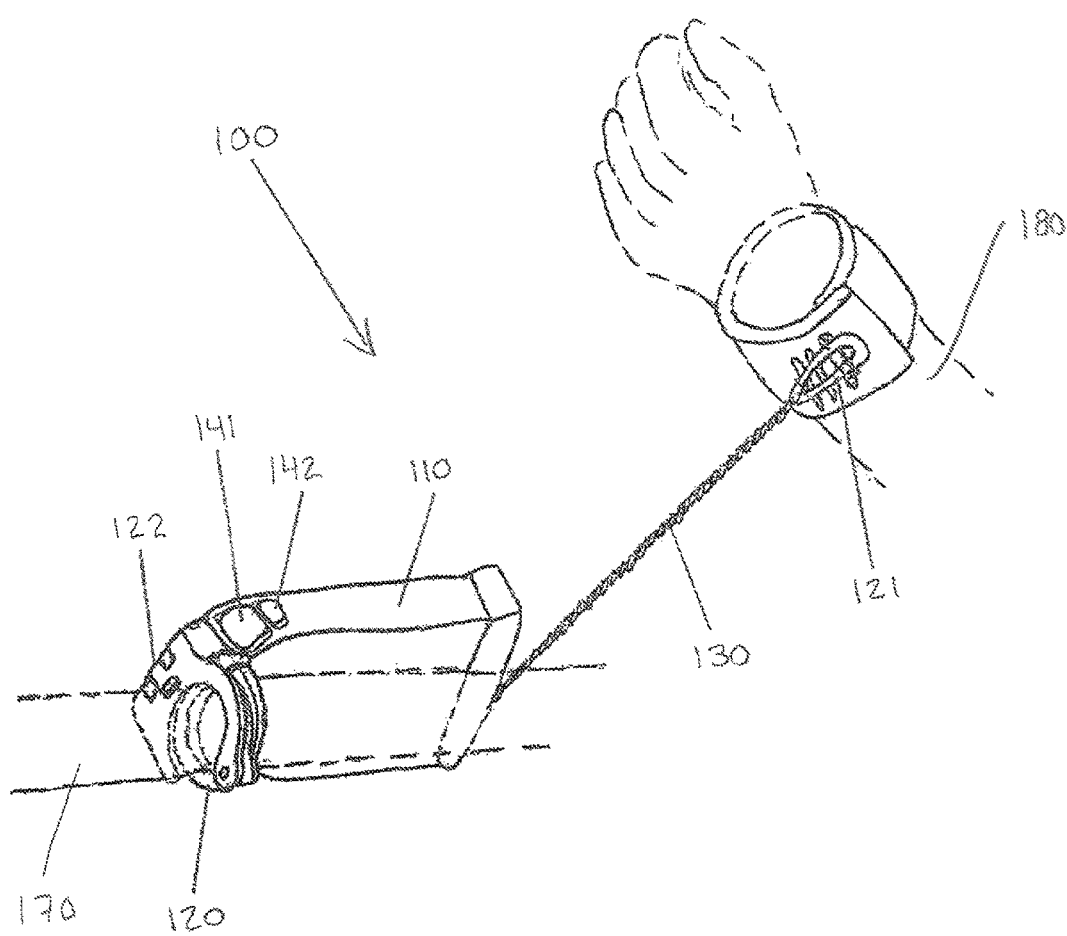
FIG. 4 is a perspective view of the restraint device illustrated in FIG. 1 engaged with a portion of a person's anatomy using a restraint.
Figure 5:
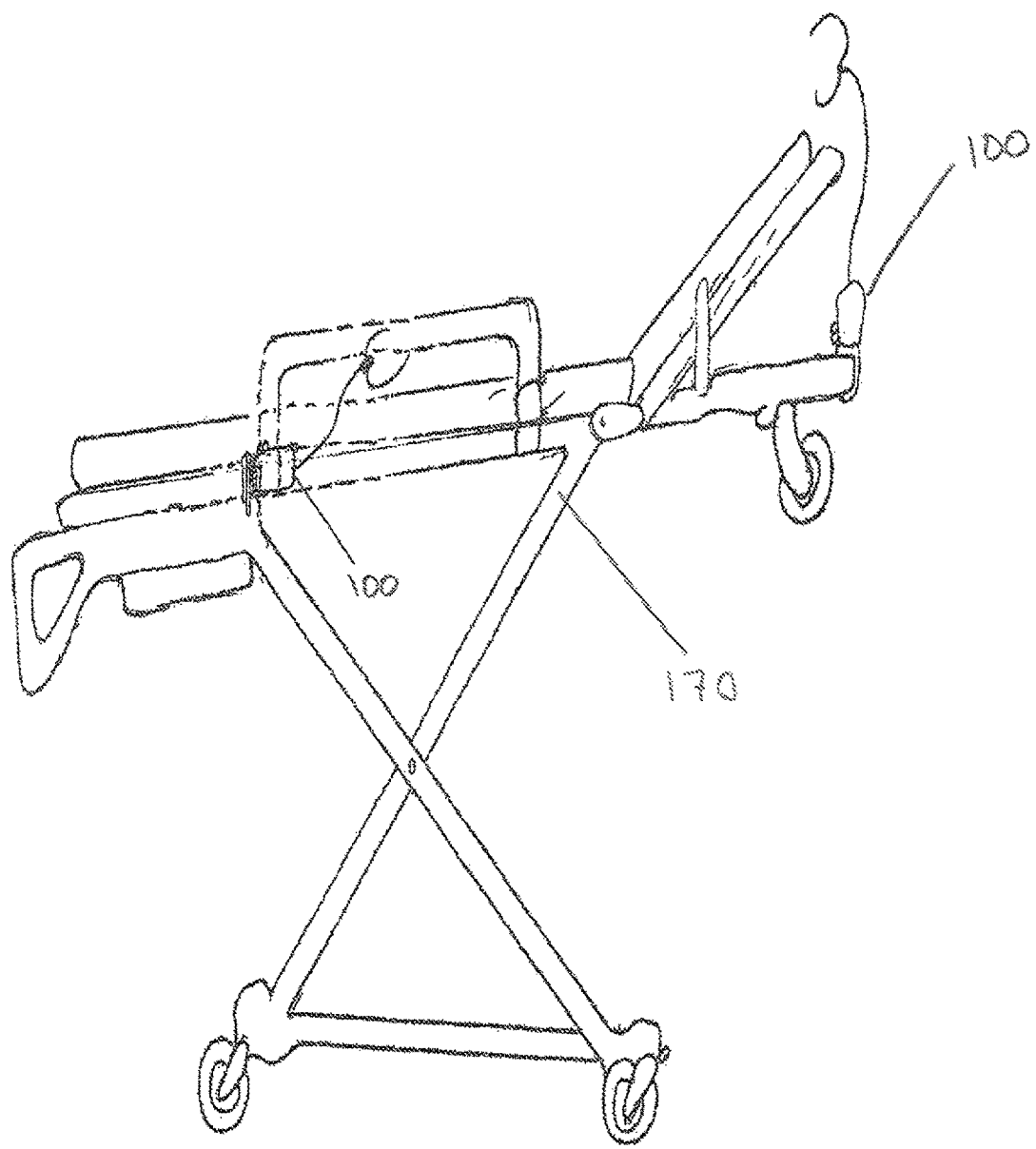
FIG. 5 is a side elevation view of the restraint device illustrated in FIG. 1 and connected to an external device.

The present invention will now be described fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art will realize that the following embodiments of the present invention are only illustrative and are not intended to be limiting in any way. Other embodiments of the present invention will readily suggest themselves to such skilled persons having the benefit of this disclosure. Like numbers refer to like elements throughout, and prime notation is used to denote similar elements in alternative embodiments of the invention.

Throughout this disclosure, the present invention may be referred to as relating to restraints, harnesses, cuffs, handcuffs, manacles, chains, and shackles. Those skilled in the art will appreciate that this terminology is only illustrative and does not affect the scope of the invention. For instance, the present invention may just as easily relate to restraints and restraint devices used in law enforcement, mental and behavioral health treatment, or the medical field. Additionally, a person of skill in the art will appreciate that the use of restraints or cuffs within this disclosure is not intended to be limited to any specific form of restraint or cuff, and should be read to apply to all forms of restraints and/or cuffs in general. Accordingly, skilled artisans should not view the following disclosure as limited to any particular restraint device, and should read the following disclosure broadly with respect to the same.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention. The terms pivot and rotation are often used interchangeably and should not be considered limiting in any way. Additionally, the terms extend and expand and the terms reduce and retract, or forms of these terms, are often used interchangeably, respectively, and should not be considered limiting in any way. Those skilled in the art will appreciate that many variations and alterations to the descriptions contained herein are within the scope of the invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

Referring to FIGS. 1-6, a restraint device 100, according to an embodiment of the present invention, is now described in detail. Throughout this disclosure, the present invention may be referred to as a restraint device 100, a cuffing system, a restraint system, a restraint, a set of restraints, a device, a system, a product, and a method. Those skilled in the art will appreciate that this terminology is only illustrative and does not affect the scope of the invention.

According to an embodiment of the present invention, as depicted, for example, in FIGS. 1-6, the restraint device 100 may include an outer body 110, a first and second connector 120, 121, and a line 130. The restraint device 100 may further include a connector member 122, a latch button 140, a locking mechanism 143, a ratchet mechanism 150, a power supply 151, and/or a storage wheel 152. The outer body 110 may include a first and second portion 111, 112. The storage wheel 152 may be a ratchet string storage wheel or other type of line 130 storage device.

The power supply 151 and other electronic circuitry may be installed into the outer body 110. Additionally, the outer body 110 may carry the latch button 140, the first and second latch buttons 141, 142, the locking mechanism 143, the ratchet mechanism 150, the power supply 151, the storage wheel 152, and the ratchet string storage wheel. The connector member 122 may pivotally or rotationally engage a portion of the outer body 110 and the first connector 120.

The line 130 may be configured to attach to the second connector 121, the ratchet mechanism 150, the power supply 151, the storage wheel 152, or the ratchet string storage wheel. The restraint device 100 may be configured so that the line 130 may be released from the outer body 110, the ratchet mechanism 150, or the power supply 151, which may allow the second connector 121 to expand away from the remaining portions of the restraint device 100, thus expanding the distance between the first and second connector 120, 121 and between the outer body 110 and the second connector 121. The line 130 may be retracted into the outer body 110 using the ratchet mechanism 150 and/or the power supply 151 in an opposite manner, thus reducing or retracting the distance between the first and second connector 120, 121 and between the outer body 110 and the second connector 121. The line 130 may girdle the ratchet mechanism 150, the storage wheel 152, and/or the ratchet string storage wheel when the line 130 has been retracted, partially retracted, locked, or while it is in storage.

The expansion or retraction described herein may be done manually, for example through manual force such as pulling the second connector 121 away from the outer body 110 and/or the first connector 120 or by manually rotating, turning, or cranking the ratchet mechanism 150, the storage wheel 152, the ratchet string storage wheel, and/or an attachment to the ratchet mechanism 150, the storage wheel 152, or the ratchet string storage wheel. The expansion or retraction may also be accomplished through use of the power supply 151, which may be a spring system, a ratcheting system, or a mechanized and/or an electronic system. The latch button 140 and/or locking mechanism 143 may allow the expansion or retraction of the line 130.

Furthermore, the latch button 140 and/or locking mechanism 143 may engage the ratchet mechanism 150 or power supply 151, which may cause the line 130 to expand, retract, or lock in relation to the outer body 110. The latch button 140 and/or locking mechanism 143 may allow the line 130 to be quickly released and/or expanded. The locking mechanism 143 may lock the line 130 or may lock the latch button 140, the first latch button 141, or the second latch button 142 thereby locking the line 130. The locking mechanism 143 may be slid, pushed, and/or pulled into the locked position and may be slid, pushed, and/or pulled in an opposite, reverse, or different direction to release and/or unlock the line 130.

The first latch button 141 may allow the line 130 to be extended, released, and/or locked in place and the second latch button 142 may allow the line 130 to be retracted, released, and/or locked in place. Additionally, the latch button 140, the first and second latch button 141, 142, or the locking mechanism 143 may increase the force necessary to release or expand the line 130 to any amount of force between near frictionless release or expansion and an amount of force required to break the line 130. As an example and without limitation, the latch button 140, the first and second latch button 141, 142, and/or the locking mechanism 143 may be engaged by applying force which may be applied by hand, finger, foot, or through any other means that may be understood by those having the benefit of this disclosure.

The ratchet mechanism 150 may include a plurality of teeth 154 that may engage with the latch button 140, the first and second latch button 141, 142, the locking mechanism 143, the power supply 151, and/or the storage wheel 152. The latch button 140, the first and second latch button 141, 142, the locking mechanism 143, the power supply 151, and/or the storage wheel 152 may include a pawl which may be a hinged or pivoted catch. The pawl may be spring-controlled or user-controlled so that once engaged, the force of the spring or user keeps the pawl engaged with the ratchet mechanism 150 and may prevent forward, reverse, or all motion of the ratchet mechanism until the pawl is released. The locking mechanism may also engage the pawl to lock the pawl in the same position. The pawl may be released or unlocked by releasing or engaging the latch button 140, the first and second latch button 141, 142, and/or the locking mechanism 143.

For example, and without limitation, when the locking mechanism 143 is engaged and the line 130 is locked or when the ratchet mechanism 150 is engaged so that the line 130 will retract, the force required to extend or expand the distance between the first and second connector 120, 121 may be greater than 200 pounds-force. Additional details regarding retraction/expansion mechanics involved in moving the line 130 between a retracted position and an extended position are available in U.S. Pat. No. 7,340,926, the entire contents of which are incorporated herein by reference.

As an additional example, and without limitation, when the latch button 140, the first and second latch button 141, 142, and/or the locking mechanism 143 are not engaged, the ratchet mechanism 150 may not be engaged and may allow the line 130 to retract and extend or expand. When the latch button 140, the first and second latch button 141, 142, or the locking mechanism 143 is engaged, or some combination of the latch button 140, the first and second latch button 141, 142, and the locking mechanism 143 is engaged, the pawl and/or the ratchet mechanism 150 may engage. When the ratchet mechanism 150 is engaged, the line 130 will not lock and will only be able to retract. If the ratchet mechanism 150 is engaged, the power supply 151 may also be engaged, thereby applying force to retract the line 130 by applying a rotational force to the ratchet mechanism 150 and/or the storage wheel 152.

In another example, and without limitation, when the latch button 140, the first and second latch button 141, 142, or the locking mechanism 143 is engaged, or some combination of the latch button 140, the first and second latch button 141, 142, and the locking mechanism 143 is engaged, the power supply 151 may apply a force to the line 130 so that the line 130 may not be able to extend, expand, or retract and the line 130 may be immobile in relation to the restraint device 100 in general. Alternatively or additionally, the power supply 151 may apply a force to the ratchet mechanism 150 and/or the storage wheel 152 so that the ratchet mechanism 150 and/or the storage wheel 152 may not rotate thereby preventing the line 130 from extending, expanding, or retracting.

In an alternative example, the line 130 may extend which may cause the power supply 151 to engage. In this manner, the power supply 151 may engage the line 130, the ratchet mechanism 150, and/or the storage wheel 152 and the line 130 may retract.

The restraint device 100 may matingly engage an external structure 170 or other object, such as a stretcher, a bed, a wheelchair, or other object. The external structure 170 may be constructed to include the restraint device 100. Additionally, a piece of rubber, plastic, foam, cloth, fabric, or other non-metallic object may be placed on the restraint device 100 and/or the external structure 170 that may reduce the noise, friction, stress and/or damage on the restraint device 100 and/or external structure 170.

For example, and without limitation, the first connector 120 may attach to the external structure. The first connector 120 may be attached to the external structure 170 by glue, adhesive, Velcro®, hook and loop fasteners, carabiner, clamp, clip, r-clip, shackle, split pin, tapered pin, latch, linchpin, lobster clasp, fastener, screw, bolt, welding, or any other means understood by those having the benefit of this disclosure. The first connector 120 may further be adjustable to more advantageously attach to many different objects or designs of stretchers, beds, or wheelchairs. The external structure 170 may include an eyelet, grommet, Velcro®, hook and loop fasteners, or other receiving portion. Additionally, the second connector 121 may attach to a restraint 190, such as a wrist cuff, a wrist restraint, a leg restraint, or other device. More specifically, the second connector 121 may attach to a ring, such as a D-ring, or other device on or attached to the restraint 190. The second connector 121 may be attached by Velcro®, hook and loop fasteners, carabiner, clamp, clip, r-clip, shackle, split pin, tapered pin, latch, linchpin, lobster clasp, fastener, screw, bolt, or any other means understood by those having the benefit of this disclosure.

As another example, and without limitation, the restraint device 100 or a portion of the restraint device 100 may be constructed with the external structure 170. The first connector 120 may be integrated into the external structure 170 through molding, integrally molding, overmolding, glue, adhesive, fastener, screw, bolt, welding, or any other means understood by those having the benefit of this disclosure. In this example, the first connector 120 may permanently connect the restraint device 100 to the external structure 170.

Also for example, and without limitation, the outer body 110 and components of the outer body 110 may be at least one of molded and overmolded, which may be individually and separately, and which may be accomplished by any molding process understood by those having the benefit of this disclosure, including, but not limited to blow molding, sintering, compression molding, extrusion molding, injection molding, matrix molding, transfer molding, and thermoforming. The outer body 110 and components of the outer body 110, such as the first and second portion 111, 112, may be attached by glue, adhesive, fastener, screw, bolt, welding, or any other means understood by those having the benefit of this disclosure.

Additionally, and without limitation, at least one of the outer body 110, components of the outer body 110, and the first and second portion 111, 112 may be provided by a material having a thermal conductivity=150 Watts per meter-Kelvin, a material having a thermal conductivity=200 Watts per meter-Kelvin, aluminum, an aluminum alloy, a magnesium alloy, a metal loaded plastics material, a carbon loaded plastics material, a thermally conducting ceramic material, an aluminum silicon carbide material, and a plastic.

The outer body 110 may be formed into any cubical or tubular shape, including a square, rectangle, circle, ovoid, triangle, or any other polygon. Referring to an embodiment of the restraint device 100, the outer body 110 may be substantially hollow to form a chamber that may be internal to the structure, for the sake of clarity, it is partially shown in FIG. 2, but does not necessarily indicate the location of the chamber or the components within. The chamber may be configured to permit the latch button 140, the first and second latch buttons 141, 142, the locking mechanism 143, the ratchet mechanism 150, the power supply 151, the storage wheel 152, and the ratchet string storage wheel to be positioned therewithin.

The chamber may present a void of sufficient geometry to permit electrical connectors, such as wires, to pass therethrough from the power supply 151 to the latch button 140, the first and second latch button 141, 142, the locking mechanism 143, and the ratchet mechanism 150 or between any of these components. In order to maintain a fluid seal between the circuitry chamber and the environment external to the restraint device 100, the outer body 110 may further include a sealing member. The sealing member may include any device or material that can provide a fluid seal as described above. For example, and without limitation, the sealing member may form a fluid seal between the first and second portion 111, 112. Other embodiments may have the chamber disposed on other parts of the outer body 110.

The restraint device 100 may be configured to further include a driver circuit and a communication device. The driver circuit may be electrically coupled to the connector member 122, the latch button 140, the first and second latch button 141, 142, the locking mechanism 143, the ratchet mechanism 150, the power supply 151, and/or the communication device. The communication device may be electrically coupled to the connector member 122, the latch button 140, the first and second latch button 141, 142, the locking mechanism 143, the ratchet mechanism 150, the power supply 151, and/or the driver circuit. The communication device may be a wireless communication device. The communication device may be a radio device, a computer network device, a visible light device, an acoustic device, or any other device understood by those having the benefit of this disclosure that provides wireless communication. Those skilled in the art will appreciate that a communication device being incorporated into the restraint device 100 advantageously allows for the restraint device 100 to be remotely operated and/or monitored, if so desired by a user. For example, a remote control may be used to rotate and/or pivot the restraint device 100, to expand or retract the second connector 121, to expand or retract the line 130, and/or to allow the second connector 121 to expand or retract.

The connector member 122 may be configured to rotate about a rotational axis defined by a horizontal axis of the restraint device 100 that passes through a portion of the outer body 110 located at an end of the outer body 110. More specifically, the rotational axis preferably perpendicularly passes through a vertical axis of the outer body 110. Although the rotational axis may pass perpendicularly through a vertical axis of the outer body 110, those skilled in the art will readily appreciate that this is simply exemplary in nature, and the rotational axis may be positioned anywhere on the restraint device 100 or the first and second connector 120, 121 that allows for the outer body 110 or the first connector 120 to be rotated as described herein.

Figure 6:
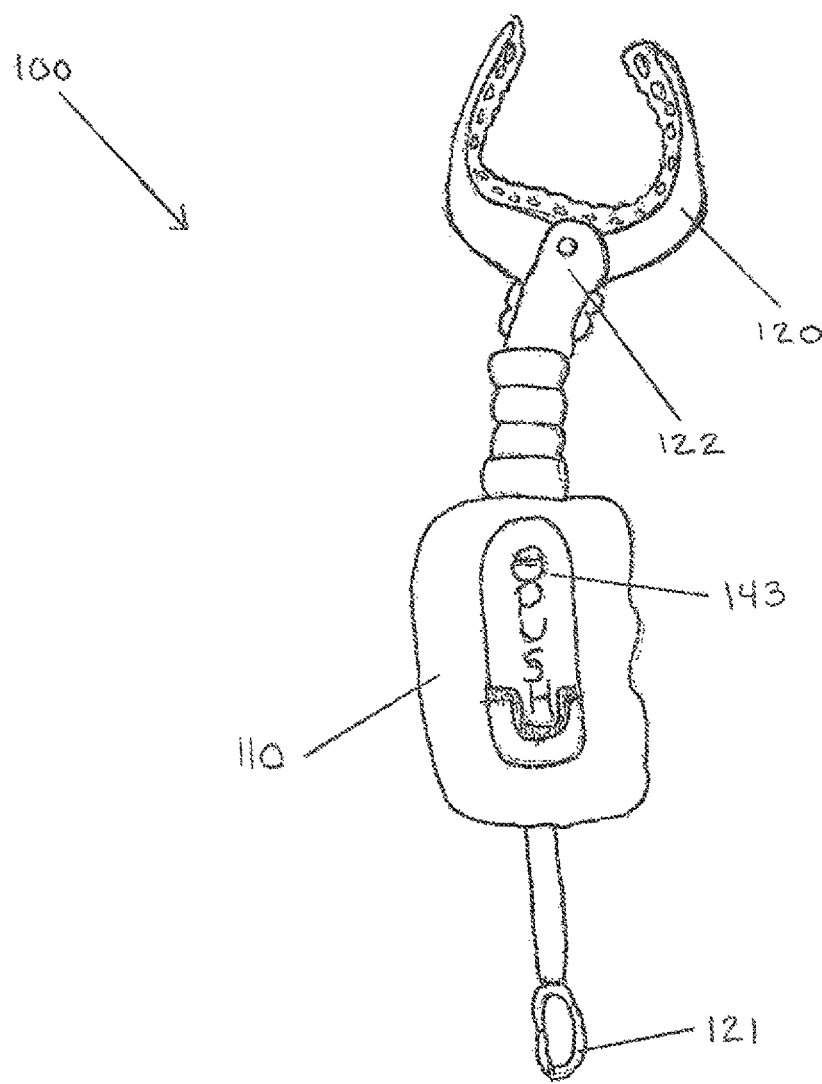
FIG. 6 is a side perspective view of a restraint device according to an alternate embodiment of the present invention.
Figure 10:
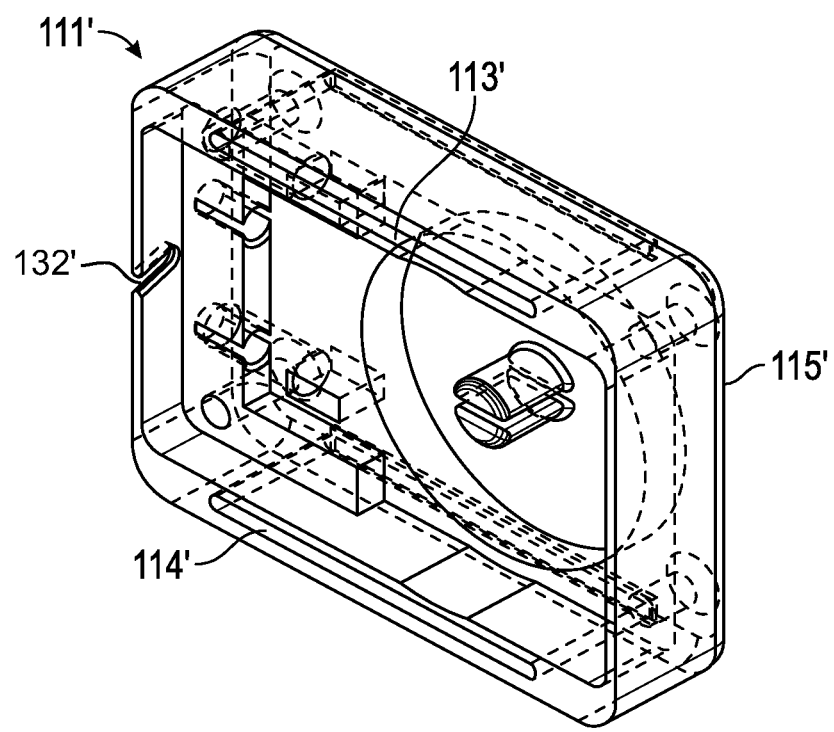
FIG. 10 is a perspective view of the first portion of the outer body of the restraint device illustrated in FIG. 7.

Those skilled in the art will appreciate that although the connector member 122 is illustrated as being a knuckle or pin joint, the connection between the outer body 110 and the first connector 120 may be provided by any means available in the art and by one or more connections. Specifically, the connection may be provided by a pivot joint, a ball and socket joint, a rotational joint, a knuckle joint, a turnbuckle, and/or a pin joint, but any joint understood by those having the benefit of this disclosure may be used. As illustrated in FIG. 6, the connector member 122 may also be connected using a combination of a neck and a joint as described herein. The neck could be flexible and may be steel, metal, metal alloy, plastic, nylon, synthetic material, fibrous material, or other similar material understood by those having the benefit of this disclosure. For example, and without limitation, the neck may be a modular hose system, such as an adjustable hose with a steel cable inserted within the hose. The neck may allow the connector member 122 to be located further away from the outer body 110 of the restraint device 100. This may also advantageously allow the outer body 110 to be positioned in a location away from the external structure 170 and allow the restraint device 100 to attach to many different objects or designs of stretchers, beds, or wheelchairs.

Those skilled in the art will further appreciate that the line 130 may be attached to the ratchet mechanism 150, the power supply 151, and/or the storage wheel 152 by any means understood by those having the benefit of this disclosure. For example, and without limitation, the line 130 may include a loop at one end that may girdle a portion of the ratchet mechanism 150, the power supply 151, and/or the storage wheel 152 or may attach to a pin or bar attached to the ratchet mechanism 150, the power supply 151, and/or the storage wheel 152. The line 130 may also be attached to the ratchet mechanism 150, the power supply 151, and/or the storage wheel 152 by compression through use of a screw, a bolt, or other device.

In one embodiment, the first connector 120 may be attached to an end portion of the outer body 110 by the connector member 122, which may be a knuckle or pin joint providing rotation of the outer body 110 and in about 270 degrees about the rotational axis. In another embodiment, the connection member 122 may be a fixed member that does not rotate. In yet another embodiment, the connection member 122 may be lockable into a position of rotation, for example in a position 30 degrees from a vertical axis of the outer body 110.

The connection member 122 preferably provides a pivot point between the first connector 120 and the outer body 110. Accordingly, and as perhaps best illustrated in FIG. 4, the first connector 120 may be connected to the external structure 170, which may be a structural item such as, for example, a railing of a stretcher, and the outer body 110 may pivot with respect to the first connector 120 so that the outer body 110 is positioned adjacent to the external structure 170, railing, or other object. The connection member 122 of the restraint device 100 according to an embodiment of the present invention advantageously allows the main body 110 of the restraint device 100 to be moved or located out of the way of the patient that is being restrained so as to enhance comfort.

The power supply 151 may be provided by a spring, a battery, an AC motor, a DC motor, an electrostatic motor, a servo motor, a stepper motor, an actuator, a hydraulic motor, a pneumatic motor, an electromagnet, or a permanent magnet. The skilled artisan will appreciate that any device suitable to cause expansion or retraction of the second connector 121 and/or the line 130 may be used as the power supply 151. Additionally, the skilled artisan will appreciate that any device suitable to cause rotation and pivoting about the rotational axis may be used as the power supply 151, without limitation. The power supply 151 may also include any other device that may impart a rotational, pivotal, or other similar action on the outer body 110, the first connector 120, the ratchet mechanism 150, the storage wheel 152, and/or the ratchet string storage wheel.

The line 130 may be steel, metal, metal alloy, plastic, nylon, synthetic material, fibrous material, or other similar material understood by those having the benefit of this disclosure. Additionally, the line 130 may be coated or jacketed with a material, including but not limited to, nylon, flame resistant material, high heat resistant material, rubber, urethane, plastic, or any other material understood by those having the benefit of this disclosure.

The restraint device 100 or parts of the restraint device 100 may also be easily removed or replaced. The restraint device 100 may further include a reservoir 160 inside or attached to the outer body 110 that contains a substance 161 that the line 130 may come into contact with. The substance 161 may be a material, liquid, or plasma that may have anti-bacterial, disinfecting, cleaning, or lubricating properties. This advantageously provides for the ability to readily clean the line 130 every time it is used. Readily cleaning and/or disinfecting the line 130 of the restraint device 100 is important as it allows for the restraint device 100 to be used on a number of different patients, thereby saving costs. The substance 161 may be applied when the line 130 is extending or retracting. The substance 161 may be positioned within the reservoir 160 by any means understood by those having the benefit of this disclosure. Therefore, upon retraction of the line 130, the substance 161 for cleaning and/or disinfecting may be readily applied to the line 130. This advantageously ensures that the line 130 is disinfected every time it is retracted, thereby eliminating the possibility that a "dirty" line is retracted into the outer body 110 of the restraint device 100.

For example, and without limitation, the substance 161 may be applied by brush, spray, dip, or any other means understood by those having the benefit of this disclosure. The line 130 may be routed through the reservoir 160 such as by a hinge, guide, or pulley system. When the line 130 is retracting, a triggering mechanism may engage thereby applying the substance 161 only when the line 130 is retracting. Alternatively, when the latch button 140 and/or the first and second latch button 141, 142 is engaged, the latch button 140 and/or the first and second latch button 141, 142 may trigger the application of the substance 161 to the line 130 or may engage the triggering mechanism thereby applying the substance 161 to the line 130.

As another example, and without limitation, the substance 161 may be applied to the line 130 by submerging the line 130, the ratchet mechanism 150 and/or the storage wheel 152 in the substance 161 when the line 130 is fully or partially retracted. The ratchet mechanism 150 and/or the storage wheel 152 may be located permanently within the confines of the reservoir 160 or may be positioned within the confines of the reservoir 160 when the latch button 140, the first and second latch button 141, 142, and/or the triggering mechanism is engaged or when the line 130 is being retracted, fully retracted, or partially retracted.

A quick release system may be included in the first and second connector 120, 121, the connector member 122, the line 130, the latch button 140, the first and second latch button 141, 142, and/or the locking mechanism 143. The quick release system, for example and without limitation, may be incorporated into the first and second connector 120, 121 whereby an individual may be able to readily detach or disconnect the first connector 120 from the external structure 170 or whereby an individual may be able to readily detach or disconnect the second connector 121 from the restraint 190 when the individual presses the latch button 140, the first latch button 141, or the second latch button 142 or otherwise releases, detaches, or disconnects the first connector 120 or the second connector 121. The second connector 121 may further include a quick release mechanism that may allow the quick release of the restraint device 100 from the individual.

The quick release system may allow a restrained individual the ability to move away in case of emergency or other need. The restraint 190 may not have to be removed and the line 130 may not have to be cut so the individual may be easily placed back into the restraint device 100.

Although the position of the first and second connectors 120, 121 appear in FIGS. 1-6 to be at opposite ends of the restraint device 100, those skilled in the art will readily appreciate that the configuration of the restraint device 100, including the first and second connectors 120, 121 and all other components of the restraint device 100, may be any configuration, and that the configurations described herein are exemplary configurations, and not meant to be limiting in any way. Those skilled in the art will readily appreciate that although only one line 130 is illustrated in FIGS. 1-6, any number of lines 130 may advantageously be used. Additionally, any number of connectors, latch buttons 140, or locking mechanisms 143 may be advantageously used.

Referring now to FIGS. 7-25, another embodiment of the restraint device 100' is now discussed in greater detail. This embodiment of the restraint device 100' illustratively includes an outer body 110', a storage wheel 152', a line 130', a first connector 120', a second connector 121', and a release mechanism 144'. The storage wheel 152' may be carried by an internal portion of the outer body 110'. The line 130' may be carried by the storage wheel 152' and may be moveable between an extended position and a retracted position. The outer body 110' may include a line passageway 132' and the line 130' may be positioned to be moveable between the extended position and the retracted position through the line passageway 132'. Those skilled in the art will appreciate that the line passageway 132' may be polygonal, circular, ovular, or any other shape and may be straight and/or curved. As illustrated, for example, the line passageway 132' may be curved slightly. As also illustrated, for example, the first portion 111' and the second portion 112' may include a portion of the line passageway 132' and the line 130' may be positionable through the line passageway 132'.

The retracted position may be defined as the line 130' being carried by the storage wheel 152' and positioned substantially internal to the outer body 110'. More specifically, however, the retracted position may also be defined as the line 130' having a substantial portion thereof positioned internal to the outer body 110'. In other words, those skilled in the art, after having the benefit of this disclosure, will appreciate that the present invention contemplates that the line 130' does not need to be completely retracted into the outer body 110' in order for it to be in the retracted position. Instead, the present invention contemplates that the line 130' may be positioned partially exterior to the outer body 110' while still being considered in the retracted position.

The extended position may be defined as the line 130' being at least partially carried by the storage wheel 152' and having at least a portion extending exterior to the outer body 110'. The extended position of the line 130' is meant to include a situation where the line is extended out of the outer body 110' so as to be able to be connected to the second connector 121', as will be discussed in greater detail below. Further, the extended position of the line 130' is meant to allow the second connector 121' to be connected to the restraint 190' and so that there is enough room for the restraint 190' to be extended and connected to a person.

The first connector 120' may be connected to a portion of the outer body 110' and may be adapted to be connected to at least a portion of an external structure 170'. The second connector 121' may be detachably connected to an end portion 131' of the line 130' and may be adapted to be detachably connected to a restraint 190'. The second connector 121' may further be capable of rapid disengagement from the restraint 190'. As perhaps best illustrated in FIG. 22, the function of rapid disengagement from the restraint 190' may be provided by the second connector 121' being a connector that is easily operable by a user such as, for example, a clip, a carabiner, or any other type of connector that may allow for engagement by a user with one hand to readily move the connector from a closed position to an opened position so that, when in the opened position, the second connector 121' may be readily engaged and disengaged from the restraint 190'. The release mechanism 144' may be carried by the outer body 110' and may be in mechanical communication with the storage wheel 152'.

The first connector 120' may, for example, and without limitation, be provided by hook and loop fasteners, a carabiner, a clamp, a clip, an r-clip, a shackle, a split pin, a tapered pin, a latch, a linchpin, a lobster clasp, a fastener, a screw, and a bolt. Additionally, the first connector 120' may be a steel or other a metal material, a metal alloy material, a plastic material, a nylon material, a synthetic material, and/or a fibrous material.

The release mechanism 144' may be moveable between an engaged position and a released position. The engaged position may be defined as the release mechanism 144' engaging a portion of the storage wheel 152' to prevent rotation thereof so that the line 130' may be prevented from moving between the extended position and the retracted position. The released position may be defined by the release mechanism 144' being disengaged from the storage wheel 152' so that the line 130' may be movable between the extended position and the retracted position. Furthermore, when the release mechanism 144' is in the released position, the storage wheel 152' may provide a rotational force to cause rotation thereof and retract the line 130' into the outer body 110'. Moving the release mechanism 144' into the released position advantageously allows for quick release of the line 130' to allow the portion of a person's anatomy 180' to move freely within a specified distance of the outer body 110'. Those skilled in the art will appreciate that the present invention contemplates the capability to allow for the line 130' to extend and retract within a certain range. This may be especially helpful when dealing with a situation where a user wants to allow a patient to move their arms, for example, but does not want the patient to be able to reach a certain part of their body (such as their other arm where an IV may be positioned). Accordingly, it is contemplated that the user may be able to set a maximum extended distance for the line 130' and a minimum retracted distance for the line 130'.

The quick release of the line 130' may allow a user to easily and quickly release the first connector 120' or the second connector 121', for example and without limitation, using one hand. This quick release may enable the person's anatomy 180' which may be connected to the restraint 190' or the restraint device 100' in general to allow the person's anatomy 180' to freely move within a very short period of time, for example nearly or substantially instantaneous, with the use of the quick release or release mechanism 144'. The quick release advantageously allows for the release of the line 130' so that the line may move freely up to a point where a connected end of the line 130' connected to the storage wheel 152' prevents further movement away from the outer body 110', such as in a fully extended position.

The outer body 110' may further include a first elongate passageway 113' and a second elongate passageway 114' opposing the first elongate passageway 113'. The first connector 120' may be positioned through the first elongate passageway 113' and an end of the first connector 120' may be unable to pass through the first elongate passageway 113'. In the illustrated embodiment, the first connector 120' is a strap that passes through the first elongate passageway 113' and the second elongate passageway 114'. After being passed through the first and the second elongate passageways 113', 114', the first connector 120' may thereafter engage the external structure 170'. As illustrated, the first connector 120' may include a fastener 123' (in the illustrated embodiment the hook and loop fastener) that allows for the first connector to be connected to the external structure 170'. Therefore, the first connector 120' may have a portion that connects to the outer body 110' and another portion that connects to the external structure 170'. Several other types of fasteners are contemplated by the present invention. For example, the fasteners may be snap connectors, or any other type of connector suitable for connecting the first connector 122' the external structure 170'. The first and second elongate passageways 113', 114' may be narrow passageways or larger passageways to accommodate the first connector 120'. Those skilled in the art will appreciate that any size first and second elongate passageways 113', 114' are included within the present invention.

The outer body 110' may further include a first side 116' and a second side 117' opposing the first side 116'. The first side 116' may have the first elongate passageway 113'. The second side 117' may have the second elongate passageway 114'.

The restraint device 100' may further include a pad 118' which may be attached to a back section 115' of the outer body 110'. The pad 118' may be neoprene, rubber, plastic, fabric, and/or foam. The pad 118' may be attached to the back section 115' by glue, adhesive, hook and loop fasteners, or any other means suitable for connecting the pad 118' to the back section 115' of the outer body 110'. The pad 118' advantageously enhances the connection that is made when the first connector 117' connects the outer body 110' of the restraint device 100. More specifically, the pad 118' may be provided by a non-slip material that may prevent, or minimize, slipping between the outer body 110' and the external structure 170'. Further, the pad 118' may reduce damage to the external structure 170' as it is preferably provided by a softer material than that of the outer body 110'.

The release mechanism 144' may be positioned on the outer body 110' opposite the back section 115'. The first connector 120' may include one fastener 123' which may be adapted to fasten the outer body 110' to the external structure 170'. The second connector 121' may also include one fastener 123' which may be adapted to fasten the second connector 121' to the restraint 190'. The restraint 190' may be adapted to be secured around a portion of the person's anatomy 180'. The restraint may include a restraint connector 191'. As perhaps best illustrated in FIG. 22, the restraint connector 191' may be, for example, a pin-like device that may be positioned through the restraint 190'. The restraint connector 191' may be removed from the position through the restraint 190' by pressing two halves of the restraint connector 191' together thereby allowing the restraint connector 191' to freely move through at least a portion of the restraint 190'. When the two halves of the restraint connector 191' are not pressed together, the two halves of the restraint connector 191' may prevent the restraint connector 191' from changing positions, thus keeping the restraint 190' positioned around the person's anatomy 180'. Those skilled in the art, after having the benefit of this disclosure, will appreciate that any form of connection may be used. In addition, the restraint 190' may include padding, other material, or another object to lessen the discomfort on the person's anatomy 180'.

The restraint device 100' may further include a ratchet mechanism 150' which may be connected to the storage wheel 152'. The ratchet mechanism 150' may be spring-controlled and/or user-controlled. When the ratchet mechanism 150' is engaged, the ratchet mechanism 150' may prevent motion of the line 130'. When the ratchet mechanism 150' is disengaged, the line 130' may move freely between the extended position and the retracted position. Further, the spring controlled feature of the ratchet mechanism 150' may advantageously allow for the line 130' to be kept in a particular extended position, while also allowing for the line 130' to be freely moved between the extended position and the retracted position, very similar to the operation of a seat belt, i.e., the line 130' may be configured to remain in a particular position until a force allows for the ratchet mechanism 150' to be disengaged and allow for the free movement of the line 130'.

Figure 11:
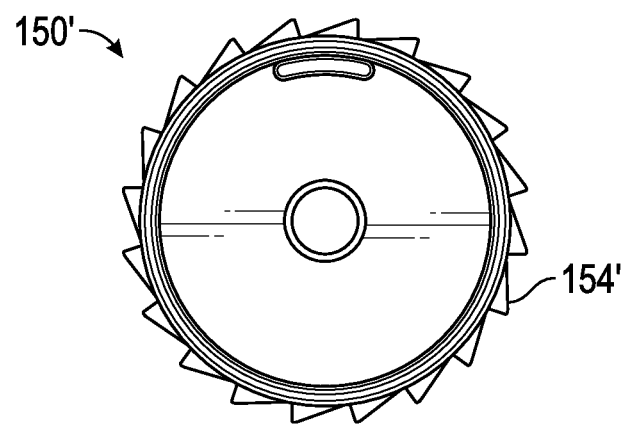
FIG. 11 is a first side elevation view of a ratchet mechanism connected to a storage wheel of the restraint device illustrated in FIG. 7.
Figure 12:
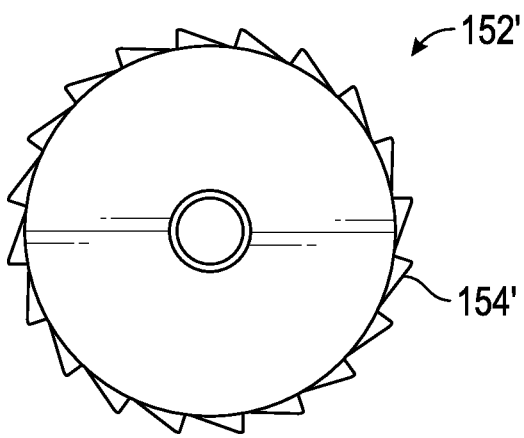
FIG. 12 is a second side elevation view of the ratchet mechanism connected to the storage wheel of the restraint device illustrated in FIG. 7.
Figure 13:
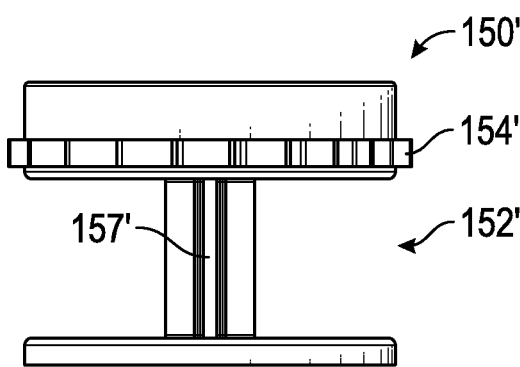
FIG. 13 is a top view of the ratchet mechanism and the storage wheel of the restraint device illustrated in FIG. 7 and showing a passageway through which a line is carried.
Figure 14:
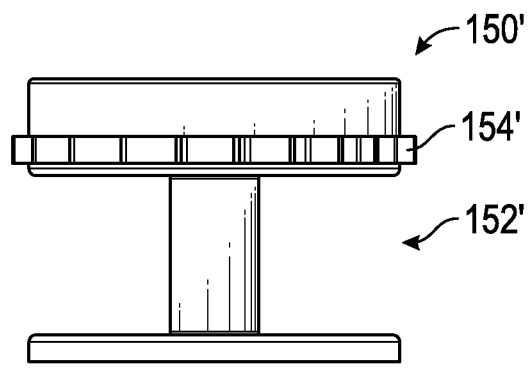
FIG. 14 is another top view of the ratchet mechanism and the storage wheel of the restraint device illustrated in FIG. 7 and showing the storage wheel in an alternate orientation.
Figure 15:
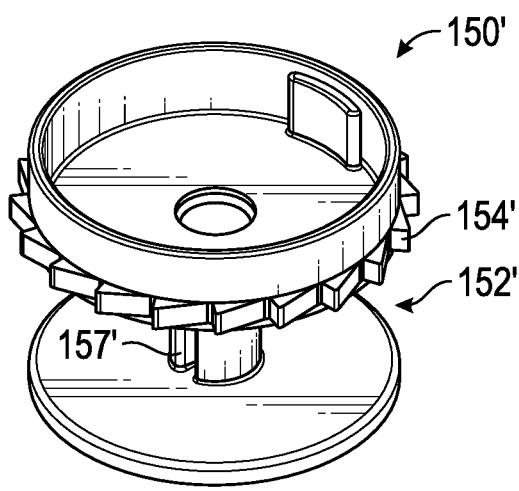
FIG. 15 is a perspective view of the ratchet mechanism and the storage wheel of the restraint device illustrated in FIG. 7.
Figure 16:
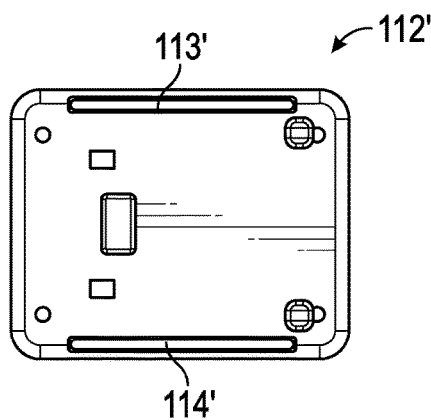
FIG. 16 is a side elevation view of a second portion of the outer body of the restraint device illustrated in FIG. 7.
Figure 17:
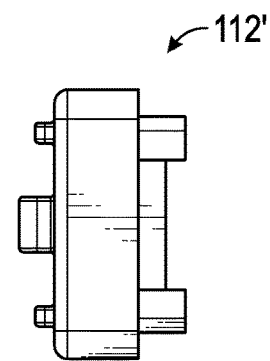
FIG. 17 is a rear elevation view of the second portion of the outer body of the restraint device illustrated in FIG. 7.
Figure 18:
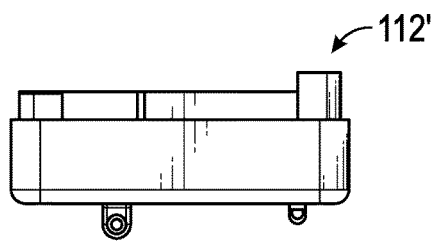
FIG. 18 is a top view of the second portion of the outer body of the restraint device illustrated in FIG. 7.
Figure 19:
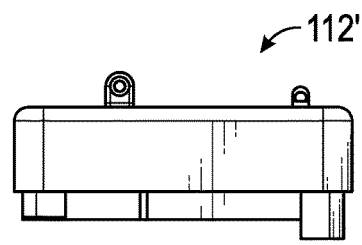
FIG. 19 is a bottom view of the second portion of the outer body of the restraint device illustrated in FIG. 7.
Figure 20:
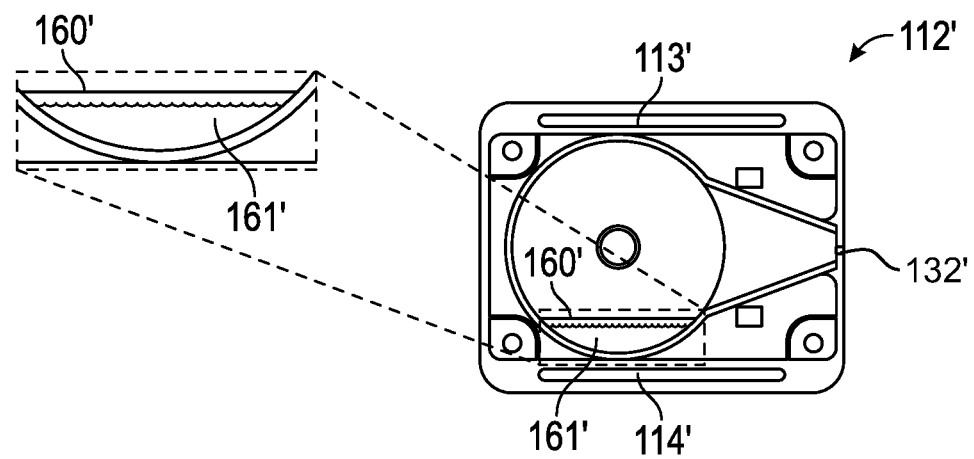
FIG. 20 is a side elevation view of the second portion of the outer body of the restraint device illustrated in FIG. 7 which further illustrates an alternative design which includes a reservoir and a substance.
Figure 21:
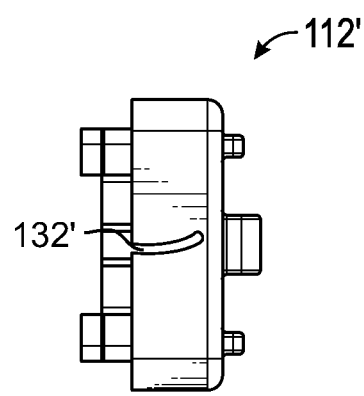
FIG. 21 is a front elevation view of the second portion of the outer body of the restraint device illustrated in FIG. 7.
Figure 22:
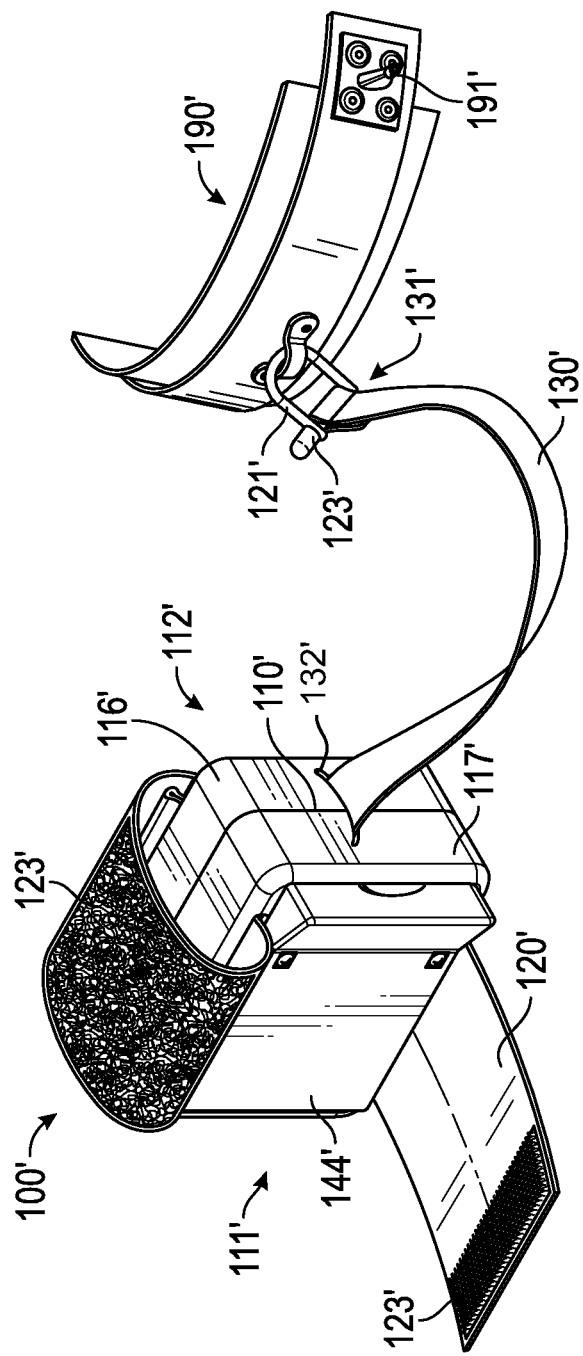
FIG. 22 is a perspective view of the restraint device illustrated in FIG. 7.
Figure 23:
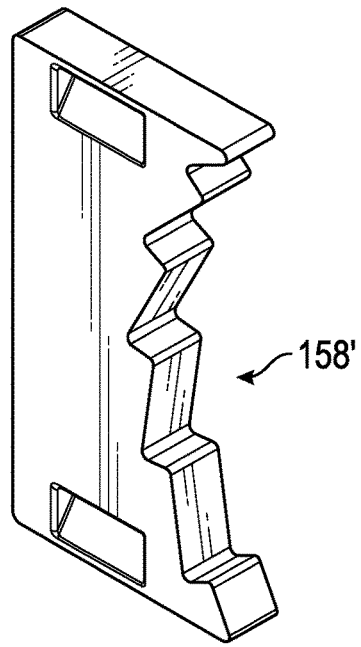
FIG. 23 is a perspective view of a portion of the ratchet mechanism of the restraint device illustrated in FIG. 7.
Figure 24:
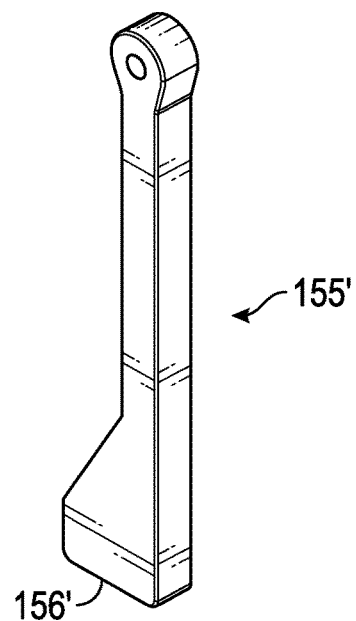
FIG. 24 is a perspective view of a portion of the release mechanism of the restraint device illustrated in FIG. 7.
Figure 25:
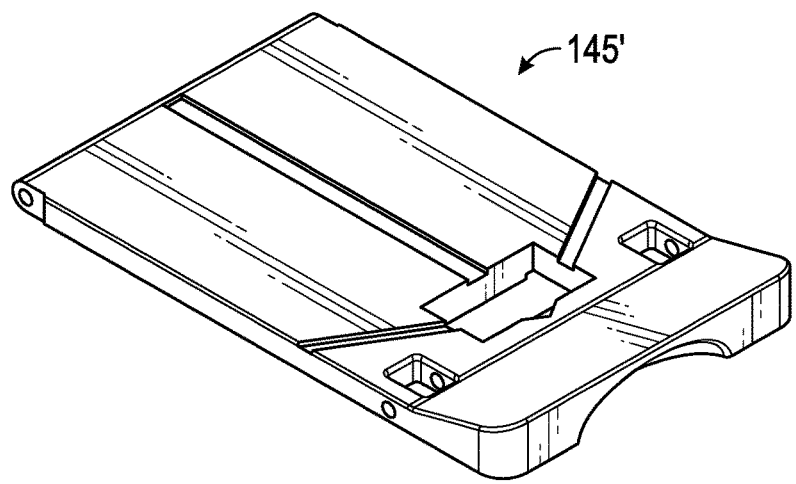
FIG. 25 is a perspective view of a portion of the release mechanism of the restraint device illustrated in FIG. 7.

As perhaps best illustrated in FIGS. 11-13, the ratchet mechanism 150' may be connected to the storage wheel 152' and may have a plurality of teeth 154'. As perhaps best illustrated in FIG. 24, a lever member 155' may be provided and may be adapted to engage a portion of the ratchet mechanism 150' and, more specifically, the plurality of teeth 154' of the ratchet mechanism 150'. Accordingly, when an end portion 156' of the lever member 155' engages an area between the plurality of teeth 154' of the ratchet mechanism 150', the end portion 156' may cause the ratchet mechanism 150' to be prevented from moving. Accordingly, since the ratchet mechanism 150' is connected to the storage wheel 150', prevention of movement of the ratchet mechanism 150' will also prevent movement of the storage wheel 152'. As perhaps best illustrated in FIG. 23, the ratchet mechanism 150' may further include a teeth engaging member 158'. The teeth engaging member 158' may be in communication with the plurality of teeth 154' so that when the ratchet mechanism 150' and/or the lever member 155' is engaged, the teeth engaging member 158' may engage the plurality of teeth 154' which may cause the ratchet mechanism 150' to be prevented from moving.

The storage wheel 152' may illustratively include a groove 157' formed therein. The groove 157' is suitable for accepting at least a portion of an end of the line 130' so as to connect the line 130' to the storage wheel 152'. To be more specific, it is contemplated that the end of the line 130' may have a width (or thickness) that is wider than the greatest width of the groove 157' to thereby allow for a sturdy connection between the storage wheel 152' and the line 130'.

The line 130' may be a steel material, a metal material, a metal alloy material, a plastic material, a nylon material, a synthetic material, and/or a fibrous material. The line 130' may be coated with a nylon, a flame resistant material, a high heat resistant material, a rubber, a urethane, and/or a plastic.

The restraint device 100' may further include a reservoir 160'. The reservoir 160' may be adapted to contain a substance 161' which may be deposited on at least a portion of the line 130'. The substance 161' may have anti-bacterial, disinfecting, cleaning, and/or lubricating properties. The substance 161' may be applied to the line 130' by a brush, a spray, and/or a dip. The line 130' may be routed through the reservoir 160' by a hinge, a guide, and/or a pulley system. This configuration advantageously enhances use of the restraint device 100' according to an embodiment of the present invention. More specifically, use of an anti-bacterial, especially in cases where the restraint device 100' is to be used in connection with a medical application, can prevent the spread of germs that, in turn, may decrease the risk of infection and other illnesses.

The restraint device 100' may further include a motor 153' which may be carried by the outer body 110'. A power supply 151' may be in communication with the motor 153'. The motor 153' may be in mechanical communication with the storage wheel 152'. Engagement of the motor 153' may cause the storage wheel 152' to turn which may move the line 130' between the extended position and the retracted position.

A method for using the restraint device 100' may include connecting the first connector 120' to the external structure 170'. The method may also include connecting the second connector 121' to a restraint 190', and moving the release mechanism 144' between the engaged position and the released position. In another embodiment, the method may include moving the first connector 120' which may be connected to a portion of the outer body 110' between an open and a closed position. The open position may be defined as the first connector 120' not being closed around the external structure 170'. The closed position may be defined as the first connector 120' being closed around the external structure 170'.

The method may further include moving a second connector 121' which may be connected to the end portion 131' of the line 130' and may be connected to the restraint 190' between an open and a closed position. The open position may be defined as the second connector 121' not being closed around the restraint 190'. The closed position may be defined as the second connector 121' being closed around the restraint 190'. The method may yet further include moving the release mechanism 144' which may be carried by the outer body 110' and in mechanical communication with a storage wheel 152' between an engaged position and a released position. The engaged position may be defined as the release mechanism 144' engaging a portion of the storage wheel 152' which may prevent rotation thereof so that the line 130' may be prevented from moving between the extended position and the retracted position.

The released position may be defined by the release mechanism 144' being disengaged from the storage wheel 152' so that the line 130' may be movable between the extended position and the retracted position. The restraint device 100' may be capable of holding at least a portion of a person's anatomy 180' in place or substantially close to the outer body 110' when the release mechanism 144' is in the engaged position. Moving the release mechanism 144' into the released position may quickly release the line 130' to allow the at least the portion of the person's anatomy 180' to move freely within a specified distance of the outer body 110'.

The method of using the restraint device 100' may further include engaging the motor 153' which may be carried by the outer body 110'. The motor 153' may be in communication with the power supply 151' and may be in mechanical communication with the storage wheel 152'. Engagement of the motor 153' may cause the storage wheel 152' to turn to move the line 130' between the extended position and the retracted position. The method of using the restraint device 100' may yet further include engaging the release mechanism 144' and the motor 153' may disengage the storage wheel 152'.

Any of the elements of this embodiment of the restraint device 100' according to the present invention that have not been specifically discussed are similar to those of the previous embodiment of the restraint device 100, are labeled with prime notation, and require no further discussion herein.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of this disclosure.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention. Also, in the drawings and the description, there have been disclosed exemplary embodiments of the invention and, although specific terms may have been used, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus the scope of the invention should be determined by the appended claims and their legal equivalents, and not by the examples given.

That which is claimed is:

1. A restraint device comprising:
   an outer body;
   a storage wheel carried by an internal portion of the outer body;
   a detachable tether that is carried by the storage wheel and moveable between an extended position and a retracted position, wherein the retracted position is defined as the tether being carried by the storage wheel and positioned substantially internal to the outer body, and wherein the extended position is defined as the tether being at least partially carried by the storage wheel and having at least a portion extending exterior to the outer body, and the tether including a quick release mechanism configured to readily detach or disconnect the tether from the storage wheel and the outer body;
   a quick release clamp connected to a portion of the outer body and adapted to be clamped to and released from at least a portion of an external structure or stretcher rail;
   a second connector detachably connected to an end portion of the tether and adapted to be detachably connected to a restraint; and
   a push/pull release button mechanism carried by the outer body and in mechanical communication with the storage wheel, wherein the push/pull release button mechanism is moveable between an engaged position and a released position, wherein the engaged position is defined as the push/pull release button mechanism engaging a portion of the storage wheel to prevent rotation thereof so that the tether is prevented from moving between the extended position and the retracted position, and wherein the released position is defined by the push/pull release button mechanism being disengaged from the storage wheel so that the tether is movable between the extended position and the retracted position.

2. The restraint device according to claim 1 further comprising a pad attached to a back section of the outer body; wherein the pad is at least one of neoprene, rubber, plastic, and foam.

3. The restraint device according to claim 2 wherein the push/pull release button mechanism comprises a biased push/pull release button mechanism positioned on the outer body opposite the back section wherein the biased push/pull release button can be easily accessed and moved from a disengaged position into a locked or engaged position by depressing the biased push/pull release button with knee or lower extremity allowing provider to have both hands free to control patient.

4. The restraint device according to claim 1 wherein the clamp includes at least one joint adapted to fasten the clamp to the outer body to allow for 360-degree rotation.

5. The restraint device according to claim 1 wherein the restraint is adapted to be secured around a portion of a person's anatomy.

6. The restraint device according to claim 1 further comprising a ratchet mechanism connected to the storage wheel.

7. The restraint device according to claim 6 wherein the ratchet mechanism is at least one of spring-controlled and user-controlled; wherein when the ratchet mechanism is engaged, the ratchet mechanism prevents motion of the tether.

8. The restraint device according to claim 1 wherein the tether comprises a line selected from the group of materials consisting of a steel, a metal, a metal alloy, a plastic, a nylon, a synthetic material, and a fibrous material.

9. The restraint device according to claim 1 wherein the tether comprises a line coated with at least one of a nylon, a flame-resistant material, a high heat resistant material, a rubber, a urethane, and a plastic.

10. The restraint device according to claim 1 further comprising a reservoir; wherein the reservoir is adapted to contain a substance to be deposited on at least a portion of the tether.

11. The restraint device according to claim 10 wherein the substance has at least one of anti-bacterial, disinfecting, cleaning, and lubricating properties.

12. The restraint device according to claim 1 further comprising a motor carried by the outer body and a power supply in communication with the motor; wherein the motor is in mechanical communication with the storage wheel; and wherein engagement of the motor causes the storage wheel to turn to move the tether between the extended position and the retracted position.

13. A restraint device comprising:
an outer body;
a storage wheel carried by an internal portion of the outer body;
a tether that is carried by the storage wheel and moveable between an extended position and a retracted position, wherein the retracted position is defined as the tether being carried by the storage wheel and positioned substantially internal to the outer body, and wherein the extended positron is defined as the tether being at least partially carried by the storage wheel and having at least a portion extending exterior to the outer body;
a restraint adapted to be secured around a portion of a person's anatomy;
a quick release clamp connected to a portion of the outer body and adapted to be clamped to at least a portion of an external structure and quickly released therefrom;
a second connector connected an end portion of the tether and connected to the restraint; and
a biased push/pull release button mechanism comprising first and second latch buttons carried by the outer body and in mechanical communication with the storage wheel, wherein one the latch buttons is configured to allow the tether to be extended, released and/or locked and the other of the latch buttons is configured to allow the tether to be retracted, released, and/or locked.

14. The restraint device according to claim 13 further comprising a power supply in mechanical communication with the storage wheel; and wherein engagement of the power supply causes the storage wheel to turn to move the tether between the extended position and the retracted position.

15. The restraint device according to claim 14 wherein the biased push/pull release button mechanism is capable of disengaging the power supply.

16. A restraint device comprising:
an outer body;
a storage wheel carried in the outer body;
a tether that is carried by the storage wheel and moveable between an extended position and a retracted position, wherein the retracted position is defined as the tether being carried by the storage wheel and positioned substantially internal to the outer body, and wherein the extended position is defined as the tether being at least partially carried by the storage wheel and having at least a portion extending exterior to the outer body;
a restraint adapted to be secured around a portion of a person's anatomy;
a quick release clamp connected to a portion of the outer body and adapted to be clamped to at least a portion of an external structure and quickly released therefrom, the clamp including at least one joint adapted to fasten the clamp to the outer body to allow for 360-degree rotation;
a second connector connected to an end portion of the tether and connected to the restraint; and
a push/pull release button mechanism carried by the outer body and in mechanical communication with the storage wheel, wherein the push/pull release button mechanism is moveable between an engaged position and a released position, wherein the engaged position is defined as the push/pull release button mechanism engaging a portion of the storage wheel to prevent rotation thereof so that the tether is prevented from moving between the extended position and the retracted position, and wherein the released position is defined by the push/pull release button mechanism being disengaged from the storage wheel, so that the tether is movable between the extended position and the retracted position.

17. The restraint device according to claim 16, wherein when the posh/pull release button mechanism is in the released position, the storage wheel has a rotational force exerted on it causing it to rotate.

18. The restraint device according to claim 17, further comprising a power supply in mechanical communication with the storage wheel; and wherein engagement of the power supply applies the rotation force and causes the storage wheel to rotate and move the tether between the extended position and the retracted position.

19. The restraint device according to claim 18, wherein the power supply comprises a spring.

* * * * *